US00PP18492P2

(12) United States Plant Patent
Klemm

(10) Patent No.: US PP18,492 P2
(45) Date of Patent: Feb. 19, 2008

(54) ***BRACTEANTHA* PLANT NAMED 'KLEBB05354'**

(50) Latin Name: *Bracteantha bracteata*
Varietal Denomination: KLEBB05354

(75) Inventor: Nils Klemm, Stuttgart (DE)

(73) Assignee: Klemm + Sohn GmbH + Co. KG

( * ) Notice: Subject to any disclaimer, the term of this patent is extended or adjusted under 35 U.S.C. 154(b) by 0 days.

(21) Appl. No.: 11/583,583

(22) Filed: Oct. 19, 2006

(51) Int. Cl.
*A01H 5/00* (2006.01)

(52) U.S. Cl. ..... Plt./359; Plt./263

(58) Field of Classification Search ..... Plt./359, Plt./263

See application file for complete search history.

*Primary Examiner*—Kent Bell
*Assistant Examiner*—S. B. McCormick-Ewoldt
(74) *Attorney, Agent, or Firm*—C. A. Whealy

(57) ABSTRACT

A new and distinct cultivar of *Bracteantha* plant named 'KLEBB05354', characterized by its upright, somewhat outwardly spreading and uniform plant habit; freely branching habit; early and freely flowering habit; inflorescences with red-colored involucral bracts; and strong peduncles that hold the inflorescences above the foliar plane.

1 Drawing Sheet

Botanical designation: *Bracteantha bracteata.*
Cultivar denomination: 'KLEBB05354'.

BACKGROUND OF THE INVENTION

The present invention relates to a new and distinct cultivar of *Bracteantha* plant, botanically known as *Bracteantha bracteata,* and hereinafter referred to by the name 'KLEBB05354'.

The new *Bracteantha* is a product of a planned breeding program conducted by the Inventor in Stuttgart, Germany. The objective of the program is to create and develop new *Bracteantha* cultivars with uniformly mounded plant habit, early and freely flowering habit and attractive inflorescence coloration.

The new *Bracteantha* originated from an open-pollination by the Inventor in 2002 of a proprietary selection of *Bracteantha bracteata* identified as code number V 117, not patented, as the female, or seed, parent with an unknown selection of *Bracteantha bracteata* as the male, or pollen, parent. The new *Bracteantha* was discovered and selected by the Inventor as a single flowering plant within the progeny of the stated open-pollination in a controlled environment in Stuttgart, Germany in 2003. The selection of this plant was based on its uniform plant habit, freely flowering habit and attractive inflorescences.

Asexual reproduction of the new *Bracteantha* by terminal cuttings in a controlled environment in Stuttgart, Germany since 2003, has shown that the unique features of this new *Bracteantha* are stable and reproduced true to type in successive generations.

SUMMARY OF THE INVENTION

The cultivar KLEBB05354 has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'KLEBB05354'. These characteristics in combination distinguish 'KLEBB05354' as a new and distinct cultivar of *Bracteantha:*

1. Upright, somewhat outwardly spreading and uniform plant habit.
2. Freely branching habit.
3. Early and freely flowering habit.
4. Inflorescences with red-colored involucral bracts.
5. Strong peduncles that hold the inflorescences above the foliar plane.

In side-by-side comparisons conducted in Stuttgart, Germany, plants of the new *Bracteantha* differed from plants of the female parent selection in the following characteristics:

1. Plants of the new *Bracteantha* are less vigorous than plants of the female parent selection.
2. Plants of the new *Bracteantha* and the female parent selection differ in involucral bract coloration as plants of the female parent selection have orange-colored involucral bracts.

Plants of the new *Bracteantha* can be compared to plants of the *Bracteantha* cultivar Mohave Autumn Bronze, not patented. In side-by-side comparisons conducted in Stuttgart, Germany, plants of the new *Bracteantha* differed from plants of the cultivar Mohave Autumn Bronze in the following characteristics:

1. Plants of the new *Bracteantha* flowered earlier than plants of the cultivar Mohave Autumn Bronze.
2. Plants of the new *Bracteantha* and the cultivar Mohave Autumn Bronze differed in involucral bract coloration as plants of the cultivar Mohave Autumn Bronze had dark orange-colored involucral bracts.

BRIEF DESCRIPTION OF THE PHOTOGRAPH

The accompanying photograph illustrates the overall appearance of the new *Bracteantha.* This photograph shows the colors as true as it is reasonably possible to obtain in colored reproductions of this type. Colors in the photograph may differ slightly from the color values cited in the detailed botanical description which accurately describe the colors of the new *Bracteantha*. The photograph comprises a close-up view of a typical flowering plant of 'KLEBB05354' grown in a container.

DETAILED BOTANICAL DESCRIPTION

In the following description, color references are made to The Royal Horticultural Society Colour Chart, 1995 Edition, except where general terms of ordinary dictionary significance are used. The aforementioned photograph, following observations and measurements describe plants grown in Stuttgart, Germany during the winter and spring in a glass-covered greenhouse and under conditions and practices which approximate those generally used in commercial *Bracteantha* production. During the production of the plants, day temperatures ranged from 18° C. to 22° C., night temperatures ranged from 14° C. to 18° C. and light levels ranged from 30,000 lux to 55,000 lux. Measurements and numerical values represent averages for typical flowering plants. Plants were grown in 12-cm containers and were about twelve weeks old when the photograph and description were taken.

Botanical classification: *Bracteantha bracteata* cultivar KLEBB05354.

Parentage:

*Female, or seed, parent.*—Proprietary selection of *Bracteantha bracteata* identified as code number V 117, not patented.

*Male, or pollen, parent.*—Unknown selection of *Bracteantha bracteata,* not patented.

Propagation:

*Type.*—Terminal vegetative cuttings.

*Time to initiate roots, summer.*—About ten days at 20° C. to 22° C.

*Time to initiate roots, winter.*—About 14 days at 18° C. to 20° C.

*Time to produce a rooted cutting, summer.*—About 16 days at 20° C. to 22° C.

*Time to produce a rooted cutting, winter.*—About 22 days at 18° C. to 20° C.

*Root description.*—Fine to fibrous; white in color.

*Rooting habit.*—Freely branching; dense.

Plant description:

*Plant form/growth habit.*—Upright, somewhat outwardly spreading and uniform plant habit with dense foliage and inflorescences held above the foliage on strong peduncles. Moderately vigorous growth habit.

*Plant height.*—About 28 cm to 33 cm.

*Plant diameter or spread.*—About 30 cm to 35 cm.

*Lateral branches.*—Quantity per plant: Freely branching habit with lateral branches developing potentially at every node; pinching enhances lateral branch development. Length: About 5 cm to 12 cm. Diameter: About 2 mm to 4 mm. Internode length: About 3 mm to 10 mm. Aspect: Mostly upright. Strength: Strong. Texture: Smooth, glabrous. Color: 137C.

*Foliage description.*—Arrangement: Alternate, simple, sessile. Length: About 10 cm. Width: About 1.5 cm. Shape: Lanceolate. Apex: Cuspidate. Base: Obtuse. Margin: Entire. Texture, upper and lower surfaces: Smooth, glabrous; rough. Venation pattern: Pinnate. Color: Developing foliage, upper surface: 137B. Developing foliage, lower surface: 137D. Fully expanded foliage, upper surface: 137A; venation, 137A. Fully expanded foliage, lower surface: 137D; venation, 137D.

Inflorescence description:

*Appearance.*—Rotate composite inflorescence form with lanceolate-shaped ray florets. Involucral bracts and disc florets developing acropetally on a capitulum. Inflorescences positioned above the foliage on strong peduncles. Inflorescences face mostly upright. Freely flowering habit; about two open inflorescences and about three to five developing inflorescences per lateral branch; about 24 developing and open inflorescences per plant. Inflorescences persistent.

*Fragrance.*—None detected.

*Time to flower.*—Early flowering habit; plants begin flowering about 72 days after planting. Plants flower throughout the summer in Germany.

*Post-production longevity.*—Inflorescences maintain good substance for about 12 to 14 days on the plant.

*Inflorescence bud.*—Height: About 1.4 cm. Diameter: About 1 cm. Shape: Roughly conical. Color: 187B.

*Inflorescence size.*—Diameter: About 5 cm. Depth (height): About 3 cm. Disc diameter: About 2 cm. Receptacle diameter: About 2 cm. Receptacle height: About 5 mm.

*Involucral bracts.*—Shape: Lanceolate. Length, largest bracts: About 8 mm. Width, largest bracts: About 3 mm. Apex: Cuspidate. Base: Obtuse. Margin: Entire. Texture: Smooth, glabrous; papery. Orientation: Flat to incurved. Number of involucral bracts per inflorescence: About 100 in about five whorls. Color: When opening and fully opened, upper surface: 185A; becoming closer to 45D with development. When opening and fully opened, lower surface: 185A.

*Disc florets.*—Arrangement: Massed in the center of the receptacle. Shape: Tubular; apex dentate, five-pointed. Length: About 1.5 cm. Diameter: About 1 mm. Number of disc florets per inflorescence: About 150. Color: Close to 17A.

*Phyllaries.*—Quantity per inflorescence: About 20. Length: About 1 cm. Width: About 2 mm. Shape: Linear. Apex: Acuminate. Base: Truncate, fused. Margin: Entire. Texture, upper and lower surfaces: Smooth. Color, upper and lower surfaces: Close to 137A.

*Peduncles.*—Length: About 3 cm. Diameter: About 3 mm. Strength: Strong. Aspect: Mostly upright. Texture: Rough. Color: 137D.

*Reproductive organs* (*present on disc florets only*).—Androecium: Quantity per disc floret: Numerous. Anther shape: Elliptic. Anther length: About 1 mm. Anther color: 21A. Pollen amount: Abundant. Pollen color: 21C. Gynoecium: Stigma shape: Bi-parted. Stigma color: 23C. Style color: 19D. Ovary color: 19D.

*Seeds/fruits.*—Seed and fruit production has not been observed.

Disease/pest resistance: Plants of the new *Bracteantha* have not been shown to be resistant to pathogens and pests common to *Bracteanthas.*

Temperature tolerance: Plants of the new *Bracteantha* have been observed to tolerate temperatures ranging from about 4° C. to about 36° C.

It is claimed:

1. A new and distinct *Bracteantha* plant named 'KLEBB05354' as illustrated and described.

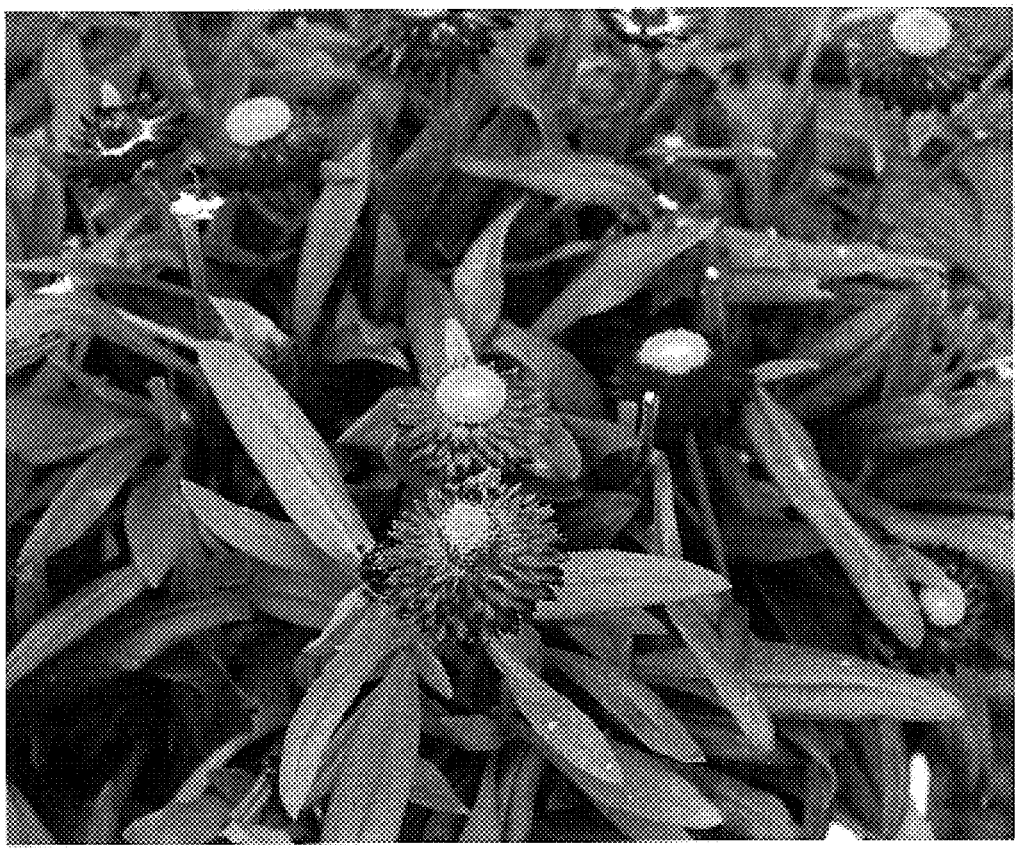

* * * * *